United States Patent
Faurissoux et al.

(10) Patent No.: US 12,085,492 B2
(45) Date of Patent: Sep. 10, 2024

(54) CENTRIFUGE ROTOR FOR CENTRIFUGING A SAMPLE, RELATED CENTRIFUGE AND MEASUREMENT METHOD

(71) Applicant: TotalEnergies OneTech, Courbevoie (FR)

(72) Inventors: Pierre Faurissoux, Pau (FR); Régis Brugidou, Gurmencon (FR); Ghislain Pujol, Higueres Souye (FR)

(73) Assignee: TotalEnergies OneTech, Courbevoie (FR)

(*) Notice: Subject to any disclaimer, the term of this patent is extended or adjusted under 35 U.S.C. 154(b) by 143 days.

(21) Appl. No.: 17/793,763

(22) PCT Filed: Jan. 23, 2020

(86) PCT No.: PCT/IB2020/000073
§ 371 (c)(1),
(2) Date: Jul. 19, 2022

(87) PCT Pub. No.: WO2021/148831
PCT Pub. Date: Jul. 29, 2021

(65) Prior Publication Data
US 2023/0061543 A1    Mar. 2, 2023

(51) Int. Cl.
*G01R 27/08* (2006.01)
*B04B 13/00* (2006.01)
(Continued)

(52) U.S. Cl.
CPC ........... *G01N 1/4077* (2013.01); *B04B 13/00* (2013.01); *G01N 15/0893* (2013.01);
(Continued)

(58) Field of Classification Search
CPC .... G01N 33/24; G01N 24/081; G01N 1/4077; G01N 15/0893; G01N 2001/4083; B04B 2013/006; B04B 13/00
See application file for complete search history.

(56) References Cited

U.S. PATENT DOCUMENTS

| 6,185,985 B1 | 2/2001 | Fleury et al. |
| 2006/0116828 A1 | 6/2006 | Chen et al. |

(Continued)

FOREIGN PATENT DOCUMENTS

| EP | 2 623 206 A1 | 8/2013 |
| FR | 2 758 881 B1 | 7/1998 |

(Continued)

OTHER PUBLICATIONS

International Search Report issued in International Patent Application No. PCT/IB2020/000073 dated Sep. 28, 2020.

Primary Examiner — Thang X Le
(74) Attorney, Agent, or Firm — TROUTMAN PEPPER HAMILTON SANDERS LLP (57) ABSTRACT

A rotor comprises a support intended to be mounted rotatable around a rotation axis in a centrifuge enclosure. The support having at least one housing for receiving the sample. At least one electrically powered sensor held by the support, configured to measure a property of the sample. A contactless power receiver, configured to receive electrical power without contact from a contactless power transmitter, the contactless power receiver being carried by the support and being jointly rotatable with the support, the contactless power receiver being electrically connected to the at least one sensor to electrically power the at least one sensor during a rotation of the support.

18 Claims, 5 Drawing Sheets

(51) Int. Cl.
*G01N 1/40* (2006.01)
*G01N 15/08* (2006.01)
*G01N 33/24* (2006.01)

(52) U.S. Cl.
CPC ........ *G01N 33/24* (2013.01); *B04B 2013/006* (2013.01); *G01N 2001/4083* (2013.01)

(56) References Cited

U.S. PATENT DOCUMENTS

| | | | |
|---|---|---|---|
| 2010/0234237 A1* | 9/2010 | Yoo | C12Q 1/686 506/7 |
| 2013/0342208 A1* | 12/2013 | Mitchell | G01N 24/081 324/309 |
| 2015/0111716 A1* | 4/2015 | Hakimuddin | G01N 33/241 494/10 |
| 2018/0071753 A1* | 3/2018 | Christian | G01N 15/1436 |
| 2020/0195104 A1* | 6/2020 | Bulatow | H02K 3/51 |

FOREIGN PATENT DOCUMENTS

| | | |
|---|---|---|
| WO | 96/19292 A1 | 6/1996 |
| WO | 96/29617 A1 | 9/1996 |
| WO | 2012/123863 A2 | 9/2012 |
| WO | 2018/193282 A1 | 10/2018 |

\* cited by examiner

CENTRIFUGE ROTOR FOR CENTRIFUGING A SAMPLE, RELATED CENTRIFUGE AND MEASUREMENT METHOD

CROSS REFERENCE TO RELATED APPLICATION

The present application is a U.S. National Phase application under 35 U.S.C. § 371 of International Patent Application No. PCT/IB2020/000073 filed Jan. 23, 2020. The entire contents of which are hereby incorporated by reference.

FIELD

The present invention concerns a centrifuge rotor for centrifuging a sample, in particular a porous sample, having:
- a support intended to be mounted rotatable around a rotation axis in a centrifuge enclosure;
- the support having at least one housing for receiving the sample;
- at least an electrically powered sensor held by the support, able to measure a property of the sample.

BACKGROUND

The centrifuge rotor is intended to be mounted in a centrifuge, for carrying out laboratory petrophysical measurements of a porous sample such as a formation sample. In particular, the measurement is associated to draining or imbibing the sample with a liquid.

The centrifuge is for example used in determining properties of the porous sample such as a relationship between the resistivity or/and conductivity and the permeability of the porous sample, such as the exponent coefficient n of Archie's Law.

FR2758881 discloses a centrifuge of the above-mentioned type. The centrifuge has a rotor able to receive rock porous samples to carry out resistivity measurements while a liquid is permeating the sample.

The sample is placed in a cell equipped with resistivity sensors, which must be electrically powered during the rotation of the porous sample in the rotor.

Thus, a rotary electrical connector is provided between the rotor and the stator of the centrifuge.

Rotary electric connectors such as disclosed in FR2758881 have many drawbacks. These drawbacks limit the use such a centrifuge for petrophysical applications which have specific constraints in terms of experiment duration and speed.

In particular, in order to obtain an efficient fluid draining, rotation at very high speeds is required.

Higher rotation speeds increase friction within the rotary connector, in which the electrical contact is usually carried out by brushes. The increased friction creates local temperature increase and mechanical wear of the brushes which can lead to defects in electrical power of the sensors, especially when the experiments lasts days, weeks or even months.

In order to overcome this difficulty, it is also known to load batteries in the rotor to power the sensors. The use of batteries avoids using a rotary electrical connector subject to friction between the rotor and the stator. Nevertheless, batteries may create unbalance limiting the rotation speed. Batteries exhaust after some time, which limit the experiment duration.

SUMMARY

One aim of the invention is to provide a centrifuge rotor for petrophysical applications, which is suitable for carrying out very long experiments at high rotations speeds.

To this aim, the invention concerns a centrifuge rotor of the above-mentioned type, characterized by a contactless power receiver, able to receive electrical power without contact from a contactless power transmitter, the contactless power receiver being carried by the support and being jointly rotatable with the support, the contactless power receiver being electrically connected to the or each sensor to electrically power the or each sensor during a rotation of the support.

The centrifuge rotor according to the invention may comprise one or more of the following feature(s), taken solely or according to any technical feasible combination:
- the contactless power receiver is an inductive coupling power receiver and/or a capacitive coupling power receiver;
- the contactless power receiver comprises a coil of wires;
- it comprises a contactless signal transmitter, to send measurements carried out by the or each sensor towards a contactless signal receiver;
- the contactless signal transmitter is an inductive coupling signal transmitter or a capacitive coupling signal transmitter, the contactless signal transmitter and the contactless power receiver advantageously having a common coil of wires;
- the support comprises a central rotatable hub, extending along the rotation axis, the contactless power receiver being carried by the central rotatable hub;
- the central rotatable hub defines a plate holder, the contactless power receiver being borne by the plate holder;
- the support comprises a bowl, the or each sample housing being received in the bowl.

The invention also comprises also relate to a centrifuge comprising:
- an enclosure defining an inner volume, a rotor as defined above, the support being mounted rotatable around a rotation axis in the inner volume of the enclosure;
- a motor able to rotate the support around the rotation axis.

The centrifuge according to the invention may comprise one or more of the followings feature(s), taken solely or according to any technical feasible combination:
- it comprises a static contactless power transmitter coupled to the contactless power receiver of the centrifuge rotor to transmit power to the contactless power receiver without contact with the contactless power receiver;
- it comprises a static contactless signal receiver, the centrifuge rotor comprising a contactless signal transmitter, coupled to the contactless signal receiver to send measurements carried out by the or each sensor towards the contactless signal receiver, without contact with the contactless signal receiver;
- it comprises a hood closing the inner volume of the enclosure, the contactless power transmitter being mounted on the hood;
- it comprises a removable cell, to hold the sample, the removable cell being removably mounted in the housing;
- the sample is a porous formation sample, in particular a rock sample.

The invention further relates to a measurement method for measuring a property of a sample, in particular a porous sample, comprising the followings steps:
- providing a centrifuge as defined above;
- placing the sample in the housing of the support;
- activating the motor to jointly rotate the support and the sample; and,
- while the support and the sample jointly rotate around the rotation axis:

transmitting power to the or each electrically powered sensor through the contactless power transmitter, to the contactless power receiver, without contact between the contactless power transmitter and the contactless power receiver;

measuring a property of the sample with the or each electrically powered sensor.

The method according to the invention may comprise the following feature:

the centrifuge comprises a static contactless signal receiver, the centrifuge rotor comprising a contactless signal transmitter, coupled to the contactless signal receiver and to the or each sensor, the method comprising sending measurements carried out by the or each sensor via the contactless signal transmitter towards the contactless signal receiver, without contact of the contactless signal transmitter with the contactless signal receiver, while the support and the sample jointly rotate around the rotation axis.

BRIEF DESCRIPTION OF THE DRAWINGS

The invention will be better understood, upon reading of the following description, given only as an example, and made in reference to the following figures in which.

DETAILED DESCRIPTION

Figure 1:
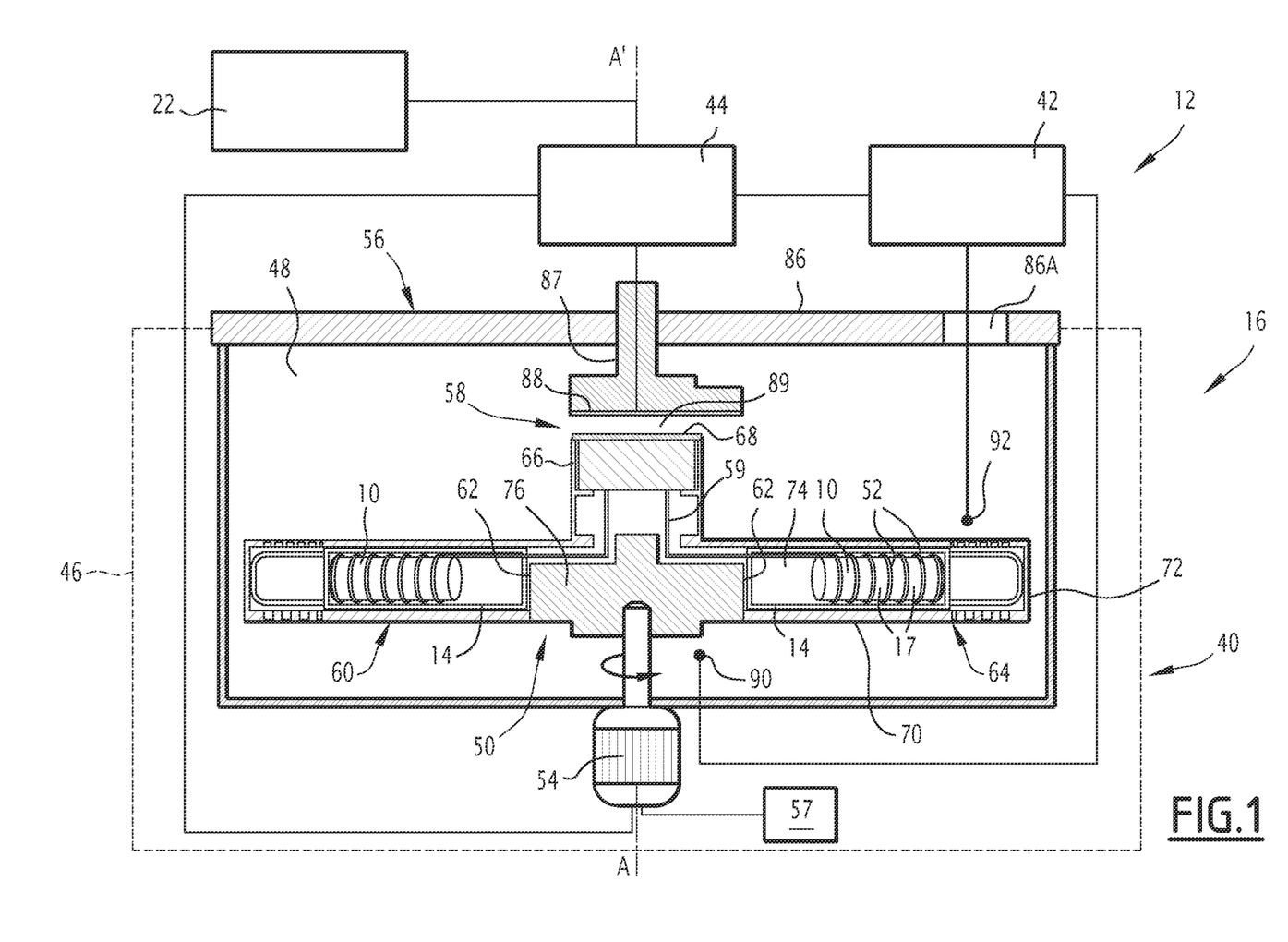
FIG. 1 is a schematic view of a measuring system including a centrifuge according to the invention.
Figure 3:
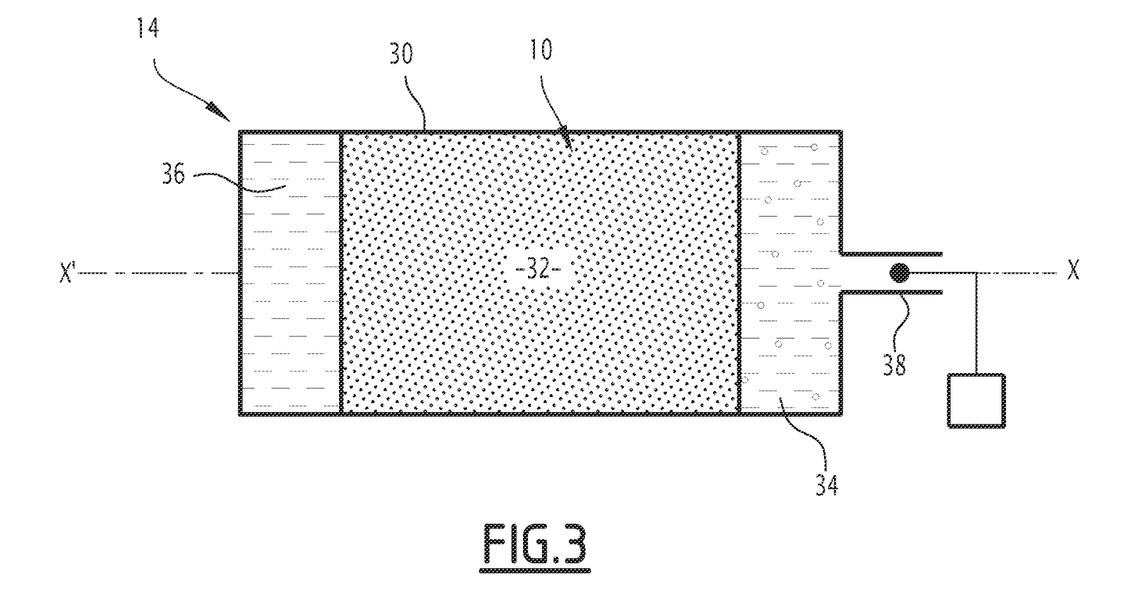
FIG. 3 is a schematic view of a cell containing a porous sample.

A centrifuge rotor 50 according to the invention is in particular used in a centrifuge 40 which is a part of a measuring system 12 illustrated in FIG. 1 for determining a representative parameter of a porous sample 10 shown in FIG. 3.

More generally, the centrifuge 40 according to the invention can be used for carrying out other petrophysical measurements in which a sample is rotated at high speeds.

The following method is therefore only one example of a measurement method involving the centrifuge 40 according to the invention, given purely as an illustration.

In this example, the representative parameter is a parameter in an equation relating at least two physical quantities associated with the porous sample 10, such as resistivity and/or conductivity on the one hand, and saturation in a first fluid of the porous sample 10, on the other hand.

Preferably, the representative parameter is the exponent saturation coefficient n in an empirical equation relating conductivity and/or resistivity to saturation in a first fluid of the porous sample 10.

The equation is for example Archie's law as defined above. In a variant, the equation is chosen among Waxman-Smits's law, Poupon-Leveaux's law, Simandoux's law, Clavier-Coates Dumanoir's Dual-Water law and/or the effective Spalburg's medium model law.

Archie's law, reformulated for electrical resistivity reads as follows:

$$R_t = a \times \phi^{-m} \times S_w^{-n} \times R_w$$

in which $R_t$ is the sample resistivity, $R_w$ is the resistivity of the brine (which depends on salinity and temperature), $\phi$ is the sample porosity, and a is a constant.

The formation factor $a \times \phi^{-m}$ is related to the resistivity of the porous sample saturated only with brine by the equation $R_0 = a \times \phi^{-m} \times R_w$. Consequently, a resistivity index RI can be determined following the following equation:

$$\log RI = \log\left(\frac{R_t}{R_0}\right) = -n \times \log S_w$$

In order to use Archie's law, the exponent coefficient n associated with the brine saturation $S_w$ has to be experimentally determined for a particular porous sample.

Simultaneously to determining the representative parameter, the method advantageously allows a determination of the relationship relating capillary pressure to saturation in a first fluid for the porous sample 10.

The porous sample 10 is for example a formation sample extracted from a sub-soil. The formation sample is in particular a rock sample having an internal porosity.

Typically, the porous sample 10 has for example a volume comprised between 8 cm³ and 60 cm³. It is advantageously cylindrical, with a circular cross-section.

The diameter of the porous sample 10 is generally comprised between 23 mm and 40 mm. Its length is for example comprised between 20 mm and 50 mm.

In a variant, the porous sample 10 is a parallelepiped.

The measuring system 12 comprises a cell 14 receiving the porous sample 10 filled with a first fluid (see FIG. 3), and a measuring apparatus 16 including a centrifuge 40 according to the invention.

In this example, the apparatus 16 is intended for establishing at least a profile, in particular a steady state profile, of a second fluid content in the porous sample 10 by applying a first mechanical load and for measuring a volume Vp of first fluid produced from the porous sample 10, when establishing the profile.

Figure 5:
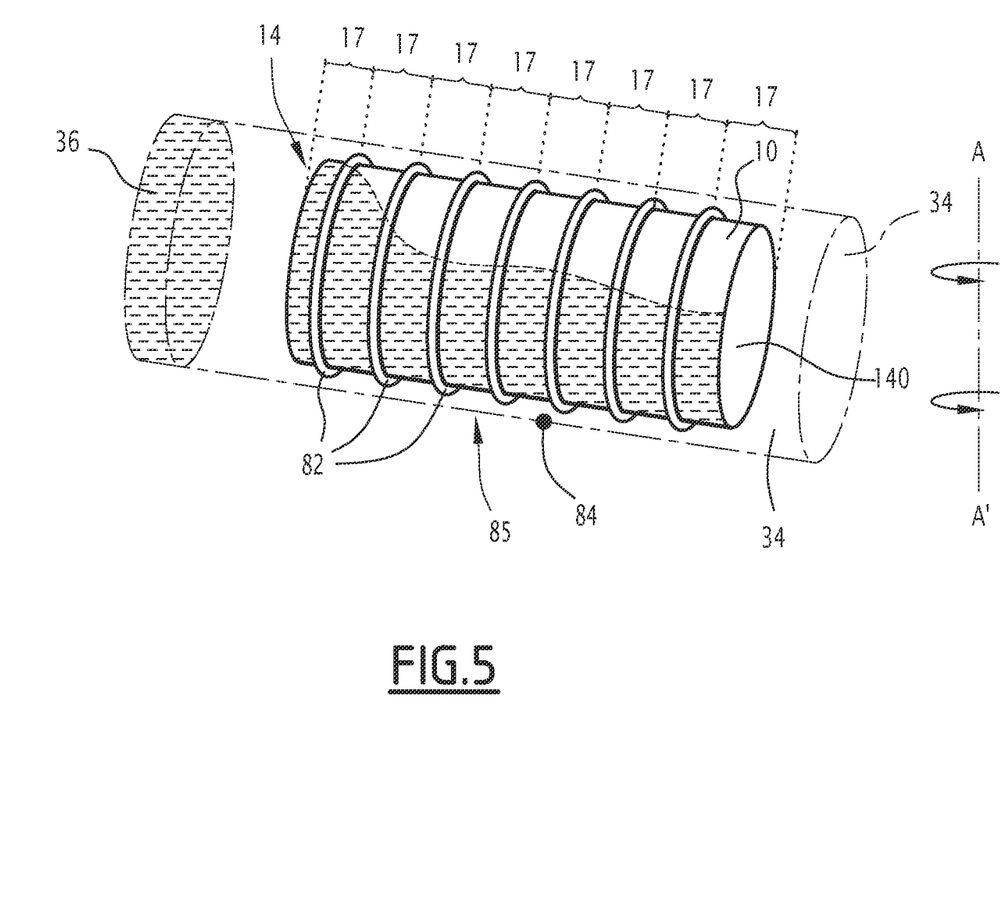
FIG. 5 is a view similar to FIG. 4, in a further step of the method.

As shown in FIG. 5, the apparatus 16 is thus able to create, in the porous sample 10, a plurality of regions 17 having different second fluid contents in the porous sample 10 and to measure, in each of the plurality of regions 17, a corresponding local electrical resistivity $R_t(i)$ and/or conductivity $C_t(i)$.

The measuring system 12 further comprises a calculator 22 for estimating a value of the total volume $VT_{1,est}$ of first fluid in the porous sample 10 from the local resistivities $R_t(i)$ and/or conductivities $C_t(i)$ measured in each region 17 and for determining the representative parameter n, based on minimizing the difference between the estimated volume $VT_{1,est}$ and a measured volume $VT_{1,mes}$ of first fluid in the porous sample 10 obtained from the measured volume Vp of first fluid produced from the porous sample 10 when establishing the steady state profile.

An example of cell 14 is shown schematically in FIG. 3. It comprises a closed enclosure 30 defining a volume 32 for receiving the porous sample 10, an upstream chamber 34, for injection of the second fluid in the porous sample 10, and a downstream chamber 36 for receiving fluids collected when a mechanical load is applied to the porous sample 10.

The cell 14 delimits at least an inlet 38 for feeding the second fluid into the upstream chamber 34. It extends along a longitudinal axis X-X' which is coaxial with the longitudinal axis of the porous sample 10.

The inlet 38 is able to be closed to seal the enclosure 30. Chambers 34 and 36 are able to fluidly communicate to equilibrate pressures when fluid is produced from the porous sample 10 in either of the chambers 34, 36 as will be described below.

The cell 14 defines at least a transparent window in the downstream chamber 36 and/or in the upstream chamber 34.

Advantageously, the enclosure 30 of the cell 14 comprises an assembly of a centrifuge cup containing the porous sample 10 and of a transparent test tube delimiting the downstream chamber 36.

Figure 2:
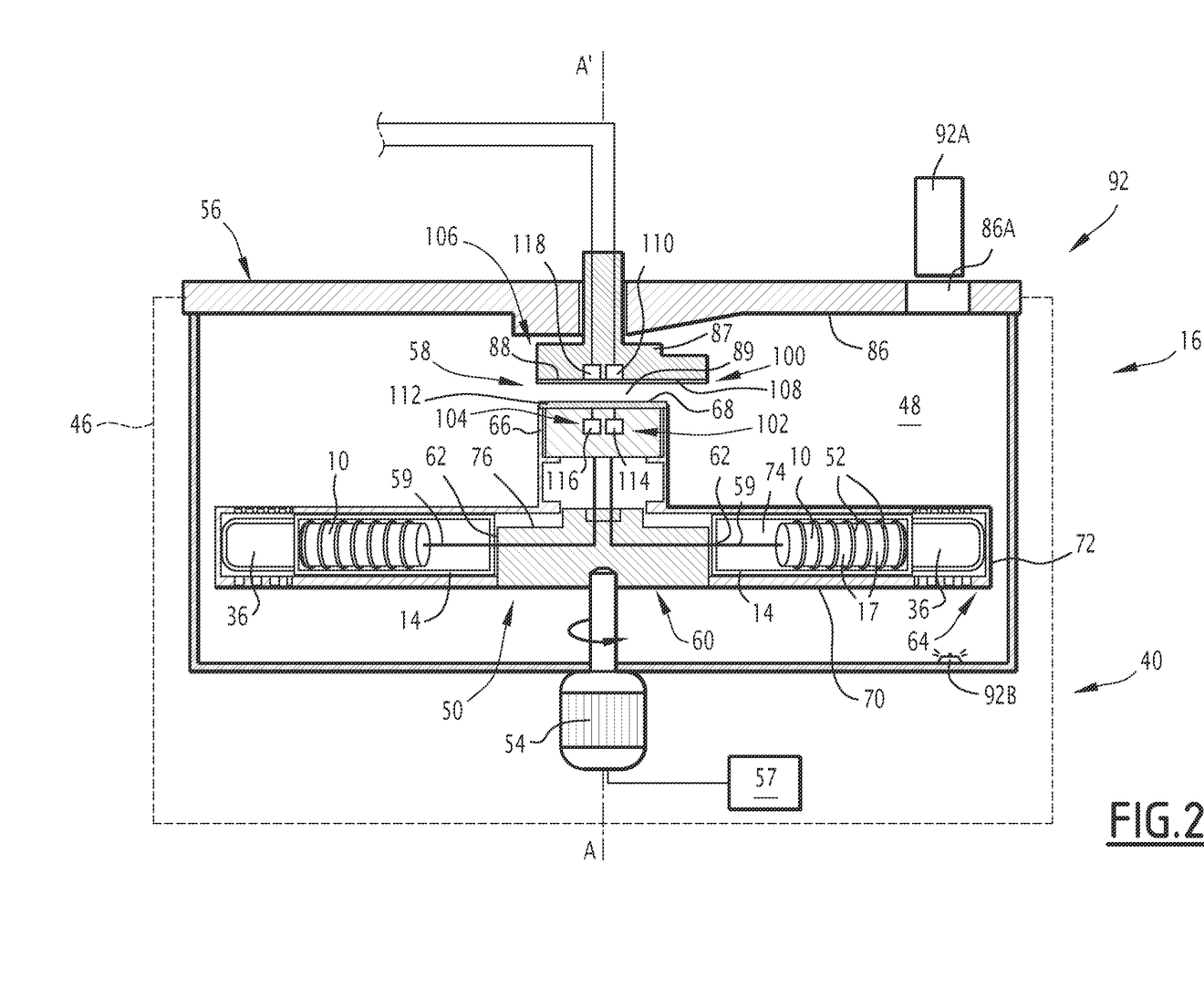
FIG. 2 is a detail of FIG. 1 showing a contactless power and signal transmission system of the centrifuge of FIG. 1.

As shown in FIGS. 1 and 2, the apparatus 16 comprises the centrifuge 40, a sensing control system 42 and a control unit 44.

The centrifuge 40 comprises an outer enclosure 46 defining an inner volume 48, and a centrifuge rotor 50 equipped with electrically powered sensors 52 to measure at least a property of the porous sample in regions 17 of the porous sample.

The centrifuge 40 further comprises a motor 54 able to drive the rotor 50 in rotation around a rotation axis A-A', a hood 56 able to close the inner volume 48, and an electrical power source 57 able to power the motor 54.

The centrifuge 40 also comprises a contactless power and signal transmission system 58 able to transmit power from the source 57 to the electrically powered sensors 52 and to transmit information from the electrically powered sensors 52 to the control unit 44 during rotation of the rotor 50 around the rotation axis A-A'. It further comprises an electrical connection 59 connecting the electrically powered sensors 52 to the contactless power and signal transmission system 58.

The enclosure 46 and the hood 56 remain static in rotation around the rotation axis A-A' when the rotor 50 rotates around the rotation axis A-A'. They will be referred to as the "static" part of the centrifuge 40 in the following description. More generally, the term "static" should be understood as static in rotation around the axis A-A' when the rotor 50 rotates. It does not prevent a movement to occur, for example of the hood 56 with regards to the enclosure 46 to allow access to the inner volume 48.

The centrifuge rotor 50 comprises a support 60 defining at least a housing 62 for receiving a porous sample 10 housed in a cell 14.

The support 60 also holds the electrically powered sensors 52 and the electrical connection 59, at least when the cell 14 is received in the housing 62.

In the example shown in FIG. 1, the support 60 comprises a bowl 64, mounted rotatable in the inner volume 48 around the axis A-A', a central hub 66 connecting the motor 54 to the bowl 64 and a rotatable holder 68 for holding a first part of the contactless power and signal transmission system 58.

The bowl 64 has a bottom wall 70 and a lateral wall 72 defining a central cavity 74 around axis A-A'. The bowl 64 is driven by the motor 54 to rotate around axis A-A' at a speed comprised between 0 rpm and 15000 rpm.

The central cavity 74 receives at least a frame 76 defining each housing 62. The frame 76 preferentially comprise arms with protrude radially from the central hub 66.

Each housing 62 extends radially with regards to the rotation axis A-A'. When received in the housing 62, in particular during rotation of the rotor 50, the axis X-X' of each porous sample 10 extends radially with regards to the rotation axis A-A'.

Figure 4:
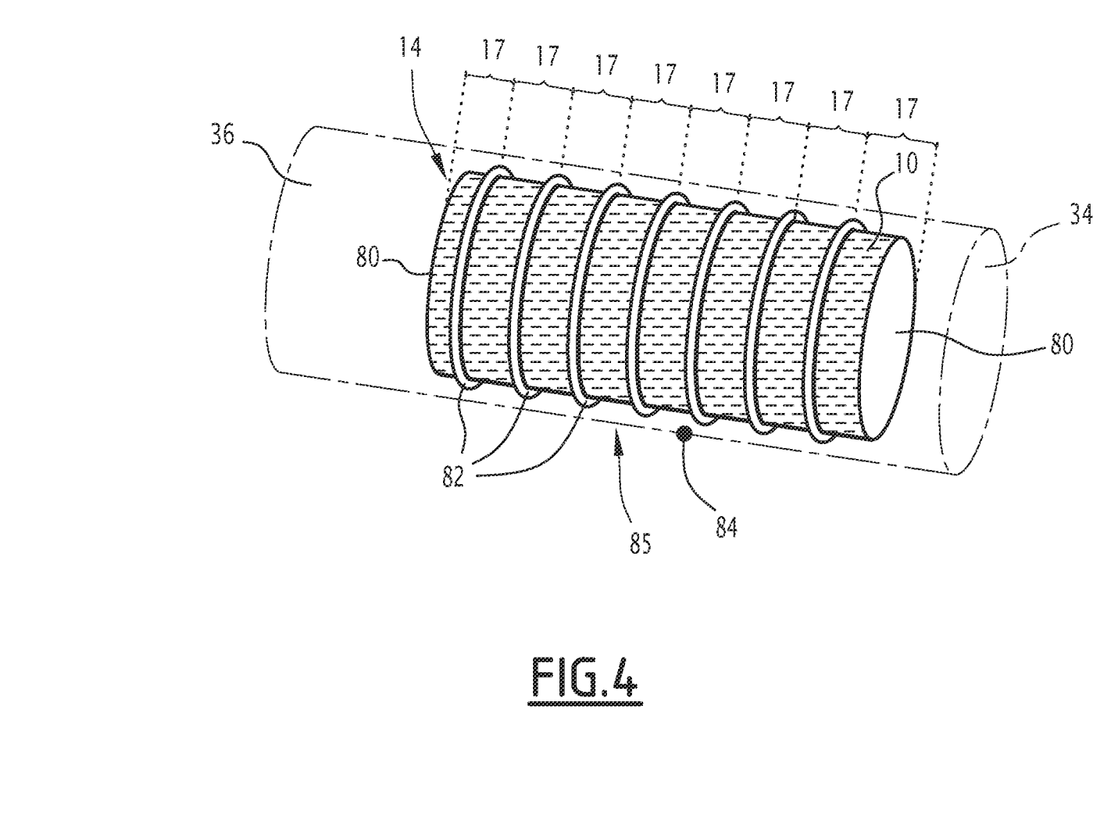
FIG. 4 is a schematic view of a sensor system comprising a plurality of resistivity probes in a preliminary step of a method carried out using a centrifuge according to the invention.

The electrically powered sensors 52 are mounted in the cell 14 around the sample 10. In the example of FIG. 4, the sensors 52 comprise at least two plate electrodes 80, mounted at the ends of the porous sample 10 and intermediate electrodes 82 each formed of at least a coil of wire, which are distributed along the length of the porous sample 10.

Each plate electrode 80 and an adjacent electrode 82, and each electrode 82 and another adjacent electrode 82 define between them a successive region 17 of the porous sample 10 in which a local resistivity $R_t(i)$ and/or conductivity $C_t(i)$ is measured by determining the tension arising between two successive adjacent electrodes 80, 82, or 82 when a current circulates in the sample 10. It may comprise a supplementary radial electrode.

In the example of FIGS. 4 and 5, the successive regions 17 are slices of the porous sample 10 taken in succession longitudinally along the length of the porous sample 10. Each slice is delimited by two parallel transverse planes which are perpendicular to the longitudinal axis X-X' of the porous sample 10. The number of regions 17 is for example comprised between 4 and 15 preferably between 7 and 11. The length of each region 17, taken along the axis is preferably smaller than 20% of the total length of the porous sample 10.

Advantageously, the electrically powered sensors 52 comprise a further sensor 84 measuring the sealing of the cell 14, for example by a resistivity measurement at the interface of the cell 14 to check that no leak occurs during centrifugation.

The electrical connection 59 comprise wires or leads connecting the electrically powered sensors 52 to the contactless power and signal transmission system 58 along the frame 76.

For example, the electrical connection 59 has at least a conductor with a first section running radially along the arms and a second section which runs axially to the rotatable holder 68.

The rotatable holder 68 preferentially has a surface which extends perpendicular to the rotation axis A-A'.

The motor 54 of the centrifuge 40 is able to be actuated by the control unit 44 to rotate the rotor 50 and jointly the cell 14 containing the porous sample 10 and the electrically powered sensors 52 at a speed of rotation ranging from 0 rpm to 15000 rpm.

A mechanical load in the form of a centrifugal force applies on the porous sample 10 and on the fluid contained in the porous sample 10. This leads to impregnation of the porous sample 10 with the second fluid contained in the upstream chamber 34 and to first fluid production in the downstream chamber 36.

The power source 57 is for example an electrical connection to an electrical network or to a generator.

The sensing unit 42 comprises a rotation speed sensor 90 able to detect the speed of rotation of the rotor 50 and a fluid production sensor 92.

The fluid production sensor 92 is able to monitor the rate of fluid production of the fluid sample 10 during rotation of the cell 14 around the rotation axis A-A'. In the example shown in FIGS. 1 and 2, the fluid production sensor 92 comprises at least a stroboscope 92B and a camera 92A able to take images of the content of the downstream chamber 36 and/or of the upstream chamber 34 along time.

The control unit 44 is able to analyze the fluid production from the images taken in the camera 92A and to relate it to a rate of production of fluid and to a volume of produced fluid $V_p$ in the downstream chamber 36 and/or in the upstream chamber 34 by image analysis.

The hood 56 comprises a door 86 able to close the inner volume 48 of the enclosure 46, and a stand 87 for receiving a second part of the contactless power and signal transmission system 58.

In this example, the hood 56 has a trough opening 86A provided through the door 86 to let the camera 92A take images of the content of the downstream chamber 36 and/or of the upstream chamber 34 along time.

In the example shown in FIG. 2, the stand 87 comprises a lower static plate 88 which protrudes transversally and perpendicularly to axis A-A', when the door 86 closes the inner volume 48.

In that position, the lower plate 88 faces the rotatable holder 68 of the centrifuge rotor 50, parallel to the upper surface of the holder 68.

An air gap 89 is defined between the lower plate 88 and the rotatable holder 68. The gap 89 for example has a height of at least 0.1 mm, in particular comprised between 1 mm and 20 mm.

Thus, the rotatable holder 68 is able to rotate coaxially to the lower plate 88 around the rotation axis A-A', facing the lower plate 88, without contact with the lower plate 88.

As shown in FIG. 2, the contactless power and signal transmission 58 comprises a static contactless power transmitter 100 held by the lower plate 88 and a rotatable contactless power receiver 102 held by the rotatable holder 68.

In addition, the contactless power and signal transmission system 58 further comprises a rotatable contactless signal transmitter 104 held by the holder 68 and a static contactless signal receiver 106 held by the lower plate 88.

The contactless power transmitter 100 comprises a static antenna made of a coil of wires 108 and a first electronic card 110 able to inject electrical power from the source 57 to the static coil of wires 108.

The contactless power receiver 102 comprises a rotatable antenna made of a coil of wires 112, able to receive electrical power from the static coil of wires 108 by contactless power transmission and a second electronic card 114 able to receive electrical power from the rotatable coil of wires 112 and to distribute it to the electrically powered sensors 52.

The contactless power transmission is carried out preferentially by inductive coupling during rotation of the rotor 50 around the rotation axis A-A'.

Thus, electrical power is continuously fed to the electrical connection 59 and to the electrically powered sensor 52 during rotation of the centrifuge rotor 50 around axis A-A', without electrical contact between the rotor 50 and the static parts of the centrifuge 40. The electrical power is also provided without having to place a battery in the centrifuge rotor 50.

In this example, the contactless signal transmitter 104 comprises the same rotatable coil of wires 112 as the contactless power receiver 102 and a third electronic card 116 able to transmit electrical signals conveying measurements made by the electrically powered sensors 52.

The contactless signal receiver 106 comprises the same static coil of wires 108 as the contactless power transmitter 100, able to receive the signals which are transmitted without contact by inductive coupling from the rotative coil of wire 112 to the static coil of wire 108 and a fourth electronic card 118.

Thus, the electrical signals produced by the electrically powered sensors 52 conveying information on the sensed physical properties of the porous sample 10 are transmitted to the contactless signal transmitter 104 through the electrical connection 59, to the contactless signal receiver 106, and then to the control unit 44.

In the present case, the signals include in particular tension and current information measured between each pair of adjacent electrodes 80, 82 around the porous sample 10 and advantageously at the sealing sensor 84.

Advantageously, the control unit 44 is able to submit the porous sample 10 to a plurality of successive mechanical load levels to establish successive profiles, in particular successive steady state profiles of second fluid content in the porous sample 10.

In particular, it is able to submit the porous sample 10 to a first mechanical load at a first speed of rotation of the porous sample 44 around the rotation axis A-A' until a first steady state is reached, when the rate of fluid extraction measured by the fluid production sensor 92 becomes zero.

Then, the control unit 44 is able to submit the porous sample 10 to a second mechanical load at a second speed of rotation of the porous sample 44 around the rotation axis A-A' until a second steady state is reached when the rate of fluid extraction measured by the fluid production sensor 92 again becomes zero. The second rotation speed is greater than the first rotation speed.

The control unit 44 is able to recover resistivity and/or conductivity measurements measured by the electrically powered sensors 52 at each steady state profile j corresponding to successive increasing mechanical loads, as well as the fluid produced $V_p$, until the steady state is reached and to transmit the measured information to the calculator 22.

The calculator 22 is for example a computer having at least a processor and at least a memory containing software modules able to be carried out by the processor.

At each steady state profile j corresponding to a given mechanical load, the calculator 22 is able to assess an initial value of the exponent coefficient n, and then to calculate, in each region 17, an estimated saturation $S_{w,est}(i,j)$ of first fluid, based on the measured resistivity $R_t(i,j)$ measured in the region 17 at the current mechanical load level j, based on the initial measured resistivity $R_0$ and based on the assessed value of the exponent n.

This calculation is done by using an inverted form of the equation relating resistivity or/and conductivity to saturation in first fluid, whose exponent coefficient is sought. When Archie's law is used, the inverted equation (1) can be used:

$$S_{w,est}(i, j) = 10^{\frac{\log\left(\frac{Rt(i,j)}{R0}\right)}{-n}} \quad (1)$$

The calculator 22 is then able to calculate an estimated volume $V_{test}(i,j)$ of first fluid in the region 17 by multiplying the estimated saturation $S_{w,est}(i,j)$ by an estimated volume of pores $V_{po,est}(i)$ in the region 17.

Advantageously, the estimated volume of pores $V_{po,est}(i)$ deduced from the total volume of pores $V_{po}$ in the whole porous sample 10 divided by the number of regions 17 in which an experiment is carried out.

The total volume of pores $V_{po}$ of the sample is determined for example via pycnometry.

Then, the calculator 22 is able to estimate an estimated total volume $VT_{1,est}(j)$ of first fluid in the porous sample 10 at the steady state profile j, by summing all the estimated volumes $V_{1,est}(i,j)$ in the different regions 17.

The calculator is able to calculate a difference D(j) between the estimated volume $VT_{1,est}(j)$ and the measured volume of first fluid $VT_{1,mes}(j)$ inside the porous sample 10 at level j.

The measured volume of first fluid $VT_{1,mes}(j)$ inside the porous sample 10 at level j is equal to the initial volume $VT_{1,mes}(j-1)$ of first fluid contained in the porous sample 10 before the steady state profile j is applied minus the volume $V_p(j)$ which has been produced at the level j when the steady state is reached.

The calculator 22 is then able to calculate an objective cost function which is here the sum S of the squares of the differences $D(j)^2$.

The objective cost function here has the following form:

$$\sum_{j=1}^{Nj}\left[\sum_{i=1}^{Ne}\left\{\left(10^{\frac{\log\left(\frac{Rt(i,j)}{R0}\right)}{-n}}\right) \times V_{po,est}(i)\right\} - VT_{1,mes}(j)\right]^2 \quad (2)$$

in which Ne is the total number of regions 17, corresponding to the number of adjacent electrode pairs 80, 82 and Nj is the total number of steady states profiles corresponding to the mechanical loads to which the porous sample 10 is subjected.

Preferentially, Ne ranges from 3 to 15, notably from 7 to 11. Preferentially, Nj ranges from 1 to 10, notably from 4 to 7

Then, the calculator 22 is able to adjust the value of the estimated representative parameter n and repeat the previous calculation steps to minimize the above-mentioned objective cost function. The representative parameter n for the porous sample 10 corresponds to the value of n for which the objective cost function is minimized.

Similarly, based on the position of each region 17 along the porous sample axis, and on the rotation speed, the calculator 22 is able to calculate the capillary pressure Pc applied in each region using the following equation:

$$Pc = \frac{1}{2} \times \omega^2 \times \Delta\rho \times (r_s^2 - r_0^2) \quad (3)$$

in which $\omega$ is the rotation speed, $\Delta\rho$ is the difference of density between the first fluid and the second fluid, $r_s$ is the radius separating the region 17 from the axis of rotation A-A', and $r_0$ is the radius separating the axis of rotation A-A' from the surface of the porous sample 10 farthest (in drainage) or closest (in imbibition) to the axis of rotation A-A'.

The calculator 22 is then able to determine a plot of the capillary pressure Pc as a function of the saturation in the first fluid $S_w$, calculated in each region from the above mentioned equation (1).

A method for determining a representative parameter of a porous sample 10 using the system 12 including a centrifuge 40 according to the invention will now be described.

Initially, a dry porous sample 10 is provided. The volume of pores $V_{po}$ in the sample is evaluated by pycnometry.

The porous sample 10 is then saturated with a first fluid, in particular with a water-based fluid such as brine.

Then, the porous sample 10 filled with the first fluid is inserted into the porous sample reception volume 32 of the cell 14.

The cell 14 is introduced in the housing 62 of the centrifuge rotor 50, with the axis X-X' of the porous sample 10 extending radially with regards to the axis of rotation A-A' of the rotor 50.

A second fluid is introduced in the upstream chamber 34 located closer to axis A-A'. The second fluid is for example oil, or gas (for example air).

The electrically powered sensors 52 are powered by transmitting power from a static part of the centrifuge 40 to the rotor 50 via the contactless power and signal transmission system 58.

The resistivity $R_o$ of the porous sample 10 saturated with the first fluid is then measured, for example using the tension measured between the end electrodes 80.

Then, the control unit 54 of the centrifuge 40 is activated to actuate the motor 60 and rotate the rotor 58 jointly with the porous sample 10 contained in the cell 14 around the rotation axis A-A'. A first mechanical load applies on the porous sample 10 due to the centrifugal force applying on the porous sample 10.

The axis X-X' of the porous sample 10 extending radially with regard to the rotation axis A-A', the second fluid contained in the upstream chamber 54 progressively penetrates into the porous sample 10 to generate a profile of saturation in the second fluid which is represented schematically with curve 140 in FIG. 5. In FIG. 5, the rotation axis A-A' of the porous sample 10 is located on the right of the porous sample 10.

The fluid production sensor 92 of the sensing unit 52 is activated to measure the rate of fluid extraction from the porous sample 10 collected in the downstream chamber 36 and the volume of produced fluid $V_p$.

In a time period comprised generally between 1 hour and 10 days, a second fluid content steady state profile establishes in the porous sample 10, when the rate of fluid extraction measured by the fluid production sensor 92 becomes zero.

In the steady state profile, the porous sample 10 comprises successive regions 17 along the longitudinal axis X-X', the successive regions 17 having different local average values of saturation $S_w$, in particular increasing values of saturation in the first fluid $S_w$ along the length of the porous sample 10, taken from the end of the porous sample 10 located closer to the axis A-A' (on the right in FIG. 5) to the end of the porous sample 10 located further away from the axis A-A' (on the left in FIG. 5).

During the measurement, and at the steady stage, power is supplied to the electrical sensors 52, during rotation of the rotor 50 through the contactless power transmitter 100, by contactless transmission to the contactless power receiver 102, and then to the electrical connection 59.

The power in particular feeds the electrodes 80, 82, to allow measurement of the resistivity in each region 17 located between an electrode 80 and the adjacent electrode 82, or between two adjacent electrodes 82.

The measurement of the local resistivity $R_t(i)$ carried out between each pair of electrodes 80, 82 or 82, 82 is transmitted from each pair of electrodes 80, 82 or 82, 82 through the electrical connection 59 to the contactless signal transmitter 104 and without contact to the contactless signal receiver 106, before reaching the control unit 44.

At each steady state profile j, the calculator 22 assesses an initial value of the exponent coefficient n, and then calculates, in each region 17, an estimated saturation $S_{w,est}(i,j)$ of first fluid, based on the measured resistivity $R_t(i,j)$ measured in the region 17 at the current mechanical load level j, based on the initial measured resistivity $R_o$ and based on the assessed value of the exponent n.

This calculation is done by using an inverted form of the equation relating the resistivity to the saturation, as explained above.

The calculator 22 then calculates an estimated volume $V_{1,est}(i,j)$ of first fluid in the region 17 by multiplying the estimated saturation $S_{w,est}(i,j)$ by an estimated volume of pores $V_{po,est}(i)$ in the region 17, as determined above.

Then, the calculator 22 estimates an estimated total volume $VT_{1,est}(j)$ of first fluid in the porous sample 10 at the steady state profile j, by summing all the estimated volumes $V_{1,est}(i,j)$ in the different regions 17 and calculates a difference $D(j)$ between the estimated volume $VT_{1,est}(j)$ and the measured volume of first fluid $VT_{1,mes}(j)$ inside the porous sample 10 at level j, as explained above.

The calculator 22 is then calculates an objective cost function which is here the sum S of the squares of the differences $D(j)^2$, as defined above.

Then, the calculator 22 adjusts the value of the estimated representative parameter n to minimize the above-mentioned objective cost function.

The representative parameter n for the porous sample corresponds to the value at which the objective cost function is minimized.

The method herein described therefore allows a very simple and effective determination of the exponent coefficient n representative of a porous sample 10 by applying successive mechanical loads in a centrifuge 40 according to the invention and by measuring the produced first fluid volume and the resistivities or/and conductivities in different regions 17 along the porous sample 10.

The latter measurement is carried out continuously when operating the method, by powering the electrically powered sensors 52 in a contactless manner and by receiving data from the electrically powered sensors 52 in a contactless manner.

The method does not require a handling of the porous sample 10 during the experiment, even if successive increasing levels of mechanical load are applied to the porous sample 10. The porous sample 10 remains in the centrifuge 40 during the whole experiment.

There is no need to use external techniques to determine the saturation in first fluid in the porous sample 10.

The timeline and cost for carrying out the method according to the invention are therefore greatly reduced, while still obtaining a very wide range of data.

In a variant, only one level of mechanical load is applied to the sample.

In another variant, the information generated by the electrically powered sensors 52 carried by the rotor 50 is transmitted by a wireless transmitter independent of the contactless power transmission to the sensors 52.

In another variant, the method is carried out without necessarily establishing a steady state profile of second fluid content in the porous sample 10. The established profile is for example a transient state profile obtained by applying the mechanical load, before a steady state profile is obtained.

Thanks to the optimized centrifuge rotor 50, it is possible to continuously power the electrically powered sensors 52, which rotate jointly with the rotor 50, without having to create an electrical contact between the rotor 50 and the static part of the centrifuge 40. This allows an increase of the rotation speed of the rotor 50 while limiting friction in the system.

Moreover, the sensors 52 being continuously powered, the experiment can last as long as needed without the need of boarding heavy batteries.

The signal transmission from the sensors 52 is carried out in real time, and thus, results of the measurements can be obtained almost immediately.

This system also allows redundancy of sensors 52, and/or a variety of measurements when several sensors of different types measure different physical quantities relative to the porous sample 10.

The centrifuge rotor 50 avoids handling the porous sample 10 during the rotation and between different levels of mechanical load and hence limit the number of operations to obtain the experimental results.

The centrifuge rotor 50 can also be used to retrofit existing centrifuge 40 and can be applied to various type of porous samples 10, in particular various types of rocks (consolidated, unconsolidated). It can also be used to rotate a gel sample or a liquid sample.

The invention claimed is:

1. A centrifuge rotor to centrifuge a sample, comprising:
    a support configured to be mounted rotatable around a rotation axis in a centrifuge enclosure, said enclosure defining an inner volume;
    the support having at least one housing configured to receive the sample;
    at least one electrically powered sensor held by the support, configured to measure a property of the sample;
    a contactless power receiver, configured to receive electrical power without contact from a contactless power transmitter, the contactless power receiver being carried by the support and being jointly rotatable with the support, the contactless power receiver being electrically connected to the at least one sensor to electrically power the at least one sensor during a rotation of the support; and
    a hood closing the inner volume of the enclosure, the contactless power transmitter being mounted on the hood.

2. The centrifuge rotor according to claim 1, wherein the contactless power receiver is an inductive coupling power receiver and/or is a capacitive coupling power receiver.

3. The centrifuge rotor according to claim 1, wherein the contactless power receiver comprises a coil of wires.

4. The centrifuge rotor according to claim 1, comprising a contactless signal transmitter, to send measurements carried out by the at least one sensor towards a contactless signal receiver.

5. The centrifuge rotor according to claim 4, wherein the contactless signal transmitter is an inductive coupling signal transmitter or a capacitive coupling signal transmitter.

6. The centrifuge rotor according to claim 1, wherein the support comprises a central rotatable hub, extending along the rotation axis, the contactless power receiver being carried by the central rotatable hub.

7. The centrifuge rotor according to claim 6, wherein the central rotatable hub defines a plate holder, the contactless power receiver being borne by the plate holder.

8. The centrifuge rotor according to claim 1, wherein the support comprises a bowl, the at least one sample housing being received in the bowl.

9. A centrifuge comprising:
    an enclosure defining an inner volume, a rotor according to claim 1, the support being rotatable around the rotation axis in the inner volume of the enclosure;
    a motor configured to rotate the support around the rotation axis; and
    a hood closing the inner volume of the enclosure, the contactless power transmitter being mounted on the hood.

10. The centrifuge according to claim 9, comprising a static contactless power transmitter coupled to the contactless power receiver of the centrifuge rotor to transmit power to the contactless power receiver without contact with the contactless power receiver.

11. The centrifuge according to claim 9, comprising a static contactless signal receiver, the centrifuge rotor comprising a contactless signal transmitter, coupled to the contactless signal receiver to send measurements carried out by the at least one sensor towards the contactless signal receiver, without contact with the contactless signal receiver.

12. The centrifuge according to claim 9, comprising a removable cell to hold the sample, the removable cell being removably mounted in the housing.

13. The centrifuge according to claim 9, wherein the sample is a porous formation sample.

14. A measurement method to measure a property of a sample, comprising:
   providing a centrifuge according to claim 9;
   placing the sample in the housing of the support;
   activating the motor to jointly rotate the support and the sample; and,
   while the support and the sample jointly rotate around the rotation axis:
   transmitting power to the at least one electrically powered sensor through the contactless power transmitter, to the contactless power receiver, without contact between the contactless power transmitter and the contactless power receiver;
   measuring a property of the sample with the at least one electrically powered sensor.

15. The centrifuge rotor according to claim 1, wherein the sample is a porous sample.

16. The centrifuge rotor according to claim 5, wherein the contactless signal transmitter and the contactless power receiver have a common coil of wires.

17. The centrifuge according to claim 13, wherein the sample is a rock sample.

18. The method according to claim 14, wherein the sample is a porous sample.

* * * * *